United States Patent [19]
Cognacq

[11] 4,127,671
[45] Nov. 28, 1978

[54] P-ACETAMIDOPHENYL DIETHYLAMINOACETATE

[75] Inventor: Jean-Claude Cognacq, Garches, France

[73] Assignee: Societe Anonyme dite: HEXACHIME, Rueil Malmaison, France

[21] Appl. No.: 800,927

[22] Filed: May 26, 1977

[51] Int. Cl.² .................... A61K 31/24; C07C 103/38
[52] U.S. Cl. .................................... 424/311; 560/142
[58] Field of Search ......................... 560/142; 424/311

[56] References Cited
U.S. PATENT DOCUMENTS

| 2,795,546 | 6/1957 | Young et al. | 560/142 |
| 3,882,166 | 5/1975 | Bauman | 560/145 |

Primary Examiner—Jane S. Myers
Attorney, Agent, or Firm—Lewis H. Eslinger

[57] ABSTRACT

A p-acetamidophenol derivative which is soluble in water giving stable aqueous solutions. This derivative is p-acetamidophenyl diethylaminoacetate, optionally in the form of a non-toxic pharmaceutically acceptable acid addition salt, particularly the hydrochloride. This derivative rapidly releases the para-acetamidophenol in the organism.

6 Claims, No Drawings

P-ACETAMIDOPHENYL DIETHYLAMINOACETATE

This invention relates to novel p-acetamidophenol derivatives, the preparation thereof and the use of such derivatives as therapeutic agents.

p-Acetamidophenol is used very frequently in therapeutics for its analgesic action, but it has the disadvantage of being practically insoluble in water.

We have sought to provide an analgesic agent which can be used in the form of aqueous solutions which are stable with the passage of time.

We have now found a novel p-acetamidophenol derivative which exhibits analgesic activity and which has the advantages of being very soluble in water to provide aqueous solutions which are stable with the passage of time.

Accordingly, the present invention provides p-acetamidophenyl diethylaminoacetate corresponding to formula (I)

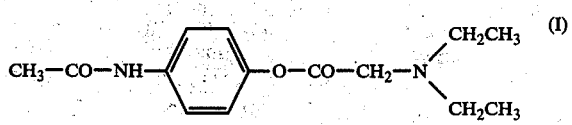

and pharmaceutically acceptable acid addition salts thereof, especially the hydrochloride.

The derivative of formula (I) and its pharmaceutically acceptable salts rapidly releases p-acetamidophenol in the organism and, therefore, these compounds are extremely effective therapeutic agents, especially analgesic agents.

Thus the invention also provides a pharmaceutical composition comprising as active ingredient p-acetamidophenyl diethylaminoacetate and/or at least one pharmaceutically acceptable acid addition salt thereof together with a pharmaceutically acceptable carrier or diluent therefor.

The invention further provides a method of preparing p-acetamidophenyl diethylaminoacetate or a pharmaceutically acceptable acid addition salt thereof which comprises reacting p-acetamidophenyl chloroacetate with diethylamine and, if desired, reacting the resulting compound of formula (I) as just defined with an acid to form a pharmaceutically acceptable and addition salt thereof.

The reaction of p-acetamidophenyl chloroacetate and diethylamine may either be carried out with an excess of diethylamine or with an equivalent amount of diethylamine in the presence of triethylamine.

The reaction is preferably carried out at a temperature of between 40° C. and 50° C. in either case.

The preparation of the p-acetamidophenol derivative according to the invention is illustrated by the following Examples.

EXAMPLE 1

22.8 g of p-acetamidophenyl chloroacetate were added in small portions to 40 c.c. of diethylamine with stirring, while the temperature was maintained at between 40° C. and 50° C. by means of a bath of cold water if necessary. When the thermal effect had ceased, the mixture was stirred for 2 hours at 45° C., cooled, poured into 250 c.c. of ice water, then extracted with ether, dried over magnesium sulphate and the ether was evaporated under vacuum to yield p-acetamidophenyl diethylamino acetate in the form of a thick oil. The base obtained in this way is used in the crude form to prepare the addition salts of acids.

For example, in order to prepare the corresponding hydrochloride, the residue was dissolved in 150 c.c. of acetone, acidified with hydrochloric acid at a pH of 1, left to settle for 1 hour, then filtered, washed with acetone, dried to obtain 13.2 g of p-acetamidophenyl diethylaminoacetate hydrochloride crystals: melting point 228° C.

EXAMPLE 2

22.8 g of p-acetamidophenyl chloroacetate were added in small portions to a solution of 7.5 g of diethylamine in 30 c.c. of triethylamine with stirring, while the temperature was maintained at between 40° C. and 50° C. with a bath of cold water if necessary. The process described in Example 1 was then followed to obtain 12 g of p-acetamidophenyl diethylaminoacetate hydrochloride melting point = 228° C.

Experiment 1

The pharmacological properties of the p-acetamidophenol derivative according to the invention are illustrated below.

The analgesic action of the product was determined by the following method: batches of 6 male mice (SPF, OFI strain), weighing 19 to 20 g, received the test product by intravenous means. 0.3 c.c. per mouse of a 0.02% solution of phenyl benzoquinone was simultaneously injected by intraperitoneal means and the number of reactions of pain (abdominal twists) was counted from the 5 to the 10 minute after the latter treatment.

The following Table I gives the inhibitory percentage of these reactions.

TABLE I

| mg/kg I.V. | % of inhibition |
|---|---|
| 8 | 26 |
| 16 | 41 |
| 32 | 68 |
| 64 | 94 |

Experiment 2

The antihyperthermisant action of the product according to the invention was determined by the following method: batches of 5 male Fauve de Bourgogne rabbits weighing 2 to 3 kg receive by intraveneous means 1 c.c./kg of an endotoxin solution of *Salmonella abortus* equivalent to 1 γ/kg in the physiological serum.

Two and a half hours later, the test product was administered in a physiological solution by intraveneous means.

The rectal temperature was recorded at regular intervals by an Ellab thermocouple. The probe was pressed 80 mm in.

The following Table II gives the temperatures recorded in degrees centigrade.

TABLE

| mg/kg I.V. | T − 2 h 30 mn | T.O. | T + 1 h 30 mn | T + 1 h | T + 1 h 30 mn | T + 2 h |
|---|---|---|---|---|---|---|
| 0 | 38.8° ± 0.10° | 40.9° ± 0.15° | 41.3° ± 0.08° | 41.4° ± 0.06° | 41.2° ± 0.11° | 40.8° ± 0.13° |
| 32 | 38.8° ± 0.06° | 41.1° ± 0.19° | 41.2° ± 0.16° | 41.0° ± 0.22° | 40.9° ± 0.21° | 40.7° ± 0.50° |

TABLE-continued

| mg/kg I.V. | T − 2 h 30 mn | T.O. | T + 1 h 30 mn | T + 1 h | T + 1 h 30 mn | T + 2 h |
|---|---|---|---|---|---|---|
| 64 | 38.8° ± 0.12° | 41.2° ± 0.24° | 40.8° ± 0.24° | 40.6° ± 0.19° | 40.4° ± 0.22° | 40.1° ± 0.28° |
| 128 | 38.8° ± 0.21° | 41.3° ± 0.34° | 41.2° ± 0.07° | 40.3° ± 0.22° | 40.1° ± 0.26° | 39.6° ± 0.22° |

In conclusion, the product examined has pharmacological properties which are comparable to those of paracetamol. It may be administered in capsules or in tablets containing 200 mg of active ingredient and in ampulla containing 100 mg of active principle. The daily dosage is from 3 to 6 oral doses and 100 to 300 mg by intraveneous means.

I claim:

1. A compound selected from the group consisting of p-acetamidophenyl diethylaminoacetate and pharmaceutically acceptable acid addition salts thereof.

2. A compound according to claim 1, said compound being p-acetamidophenyl diethylaminoacetate hydrochloride.

3. A pharmaceutical composition to induce analgesia consisting essentially of a physiologically effective amount of a compound selected from the group consisting of p-acetamidophenyl diethylaminoacetate and pharmaceutically acceptable acid addition salts thereof as active ingredient in conjunction with a pharmaceutically acceptable adjuvant.

4. A method of treating a human being to induce analgesia which consists of administering to the human being a physiologically effective amount of a pharmaceutical composition consisting essentially of a compound selected from the group consisting of p-acetamidophenyl diethylaminoacetate and pharmaceutically acceptable acid addition salts thereof as active ingredient in conjunction with a pharmaceutically acceptable adjuvant.

5. A method of treating a human being to induce analgesia according to claim 4, which consists of administering orally to said human being at a rate of about 3 to 6 doses per day said pharmaceutical composition in a form selected from the group consisting of capsules and tablets containing about 200 mg of said active ingredient.

6. A method of treating a human being to induce analgesia according to claim 4 which consists of administering intravenously to said human being at a rate of about 100 mg to about 300 mg of said active ingredient, said pharmaceutical composition in a form of an ampulla containing about 100 mg of said active ingredient.

* * * * *